(12) United States Patent
O'Hagan et al.

(10) Patent No.: US 7,544,476 B1
(45) Date of Patent: Jun. 9, 2009

(54) IDENTIFYING CANCERS SENSITIVE TO TREATMENT WITH INHIBITORS OF NOTCH SIGNALING

(75) Inventors: Ronan O'Hagan, Arlington, MA (US); H. Heidi Okamura, Brookline, MA (US); Alisa C. Bell, Burlington, MA (US); Jeanine Lorusso, Ashland, MA (US)

(73) Assignee: AVEO Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 12/360,790

(22) Filed: Jan. 27, 2009

Related U.S. Application Data (60) Provisional application No. 61/080,122, filed on Jul. 11, 2008.

(51) Int. Cl.
*C12Q 1/68* (2006.01)

(52) U.S. Cl. .......................................................... 435/6

(58) Field of Classification Search ........................ None
See application file for complete search history.

(56) References Cited

FOREIGN PATENT DOCUMENTS

| WO | WO-2006/047878 | 5/2006 |
|---|---|---|
| WO | WO-2006/092062 | 9/2006 |
| WO | WO-2007/136856 | 11/2007 |

OTHER PUBLICATIONS

Iso et al. "HES and HERP Families: Multiple Effectors of the Notch Signaling Pathway" (2003) *J. Cellular Physiol.* 194:237-255.
Leong et al. "Jagged1-mediated Notch activation induces epithelial-to-mesenchymal transition through Slug-induced repression of E-cadherin" (2007) *J. Experimental Med.* 204:2935-2948.
Parker et al. "Alterations in Vascular Gene Expression in Invasive Breast Carcinoma" (2004) *Cancer Research* 64:7857-7866.

*Primary Examiner*—Kenneth R. Horlick
*Assistant Examiner*—Christopher M. Babic
(74) *Attorney, Agent, or Firm*—Goodwin Procter LLP (57) ABSTRACT

The disclosure provides a method for identifying cancer tissue sensitive to treatment with an inhibitor of Notch receptor activation. The method comprises determining the level of HeyL gene expression in a sample derived from the cancer tissue, wherein an elevated level of HeyL gene expression alone in the sample indicates sensitivity to the cancer tissue to treatment with an inhibitor of Notch receptor activation.

9 Claims, 3 Drawing Sheets

IDENTIFYING CANCERS SENSITIVE TO TREATMENT WITH INHIBITORS OF NOTCH SIGNALING

CROSS-REFERENCE TO RELATED APPLICATIONS

This application claims the benefit of and priority to U.S. provisional patent application Ser. No. 61/080,122, filed Jul. 11, 2008; the entire contents of which are incorporated herein by reference.

FIELD OF INVENTION

The field of the invention is molecular biology and oncology.

BACKGROUND OF INVENTION

Most cancer drugs are effective in some patients but not others. This results from genetic variation among tumors, and can be observed even among tumors within the same patient. Variable patient response is particularly pronounced with respect to targeted therapeutics. Therefore, the full potential of targeted therapies cannot be realized without suitable biomarkers for determining which patients will benefit from which drugs. The National Institutes of Health (NIH) defines a biomarker as follows:

> A characteristic that is objectively measured and evaluated as an indicator or normal biologic or pathogenic processes or pharmacological response to a therapeutic intervention.

The development of improved diagnostics based on the discovery of biomarkers has the potential to accelerate new drug development by identifying, in advance, those patients most likely to show a clinical response to a given drug. This would significantly reduce the size, length and cost of clinical trials. Technologies such as genomics, proteomics and molecular imaging currently enable rapid, sensitive and reliable detection of specific gene mutations, expression levels of particular genes, and other molecular biomarkers. In spite of the availability of various technologies for molecular characterization of tumors, the clinical utilization of cancer biomarkers remains largely unrealized because few cancer biomarkers have been discovered. For example, a recent review article states:

> There is a critical need for expedited development of biomarkers and their use to improve diagnosis and treatment of cancer. (Cho, 2007, *Molecular Cancer* 6:25)

Another recent review article on cancer biomarkers contains the following comments:

> The challenge is discovering cancer biomarkers. Although there have been clinical successes in targeting molecularly defined subsets of several tumor types—such as chronic myeloid leukemia, gastrointestinal stromal tumor, lung cancer and glioblastoma multiforme—using molecularly targeted agents, the ability to apply such successes in a broader context is severely limited by the lack of an efficient strategy to evaluate targeted agents in patients. The problem mainly lies in the inability to select patients with molecularly defined cancers for clinical trials to evaluate these exciting new drugs. The solution requires biomarkers that reliably identify those patients who are most likely to benefit from a particular agent. (Sawyers, 2008, *Nature* 452:548-552, at 548)

Such comments illustrate the recognition of a need for the discovery of clinically useful biomarkers and diagnostic methods based on such biomarkers.

Vertebrates, including mammals, have four distinct Notch proteins, also known as Notch receptors (Notch1 to Notch4). All four Notch receptors are type 1 transmembrane proteins that include an extracellular domain, transmembrane domain, and an intracellular domain.

The Notch pathway is a highly conserved system for cell-to-cell signaling. It is present in all metazoans and plays multiple roles in normal growth and development. For a review regarding the Notch pathway, see, e.g., Ilagan et al., 2007, *Cell* 128:1245-1246. Notch function is complex and highly dependent on cellular context (temporal context, as well as anatomical context). Notch signaling is dysregulated in many cancers. Not only does Notch signaling affect a wide range of cell types and processes, Notch signaling produces opposite effects when activated in different cellular contexts. For example, Notch signaling stimulates proliferation of T cells and inhibits apoptosis, while causing cell cycle arrest and inducing apoptosis in B cells. Notch functions as an oncogene in some cellular contexts, while functioning as a tumor repressor in other cellular contexts.

Notch is a potential therapeutic target in the treatment of certain cancers. However, the complexity of Notch biology makes the effect of Notch pathway inhibition in any given tumor unpredictable. This underscores the need for discovery of a diagnostic method for identifying tumors that will respond to treatment with inhibitors of Notch signaling.

SUMMARY OF THE INVENTION

The invention is based in part on the discovery that an elevated level of HeyL gene expression in a tissue sample from certain mammalian cancers indicates sensitivity to treatment with an inhibitor of Notch receptor activation.

Accordingly, the invention provides a method of identifying a cancer tissue sensitive to treatment with an agent that inhibits Notch receptor activation. The method includes the steps of: (a) determining the level of HeyL gene expression in a sample derived from the cancer tissue; and (b) comparing the level of HeyL gene expression against a standard value, thereby identifying a cancer tissue sensitive to treatment with an agent that inhibits Notch receptor activation on the basis of HeyL gene expression alone. An elevation in HeyL gene expression in the sample indicates sensitivity of the cancer tissue to treatment with the agent. Under certain circumstances, the identifying in step (b) is not based on the expression level of any gene other than HeyL. In some embodiments of the invention, the elevation in the level of HeyL gene expression is at least two-fold, in comparison with the level of HeyL gene expression in a suitable control sample, e.g., two-fold to forty-fold, or four-fold to thirty-fold. In some embodiments of the invention, the level of HeyL gene expression level is determined by mRNA detection. In some embodiments of the invention, the mRNA detection is by microarray. In some embodiments of the invention the mRNA detection is by quantitative PCR. In some embodiments of the invention, the level of HeyL gene expression is determined by HeyL polypeptide assay.

In another embodiment, the invention provides a method of identifying a cancer tissue sensitive to treatment with an agent that inhibits Notch receptor activation wherein the method comprises the following steps: (a) obtaining a sample from a cancer tissue; (b) determining the level of HeyL gene expression in the sample; and (c) comparing the level of HeyL gene expression against a standard value, thereby identifying a cancer tissue sensitive to treatment with an agent that inhibits Notch receptor activation on the basis of HeyL gene expression alone. As described herein, an elevation in HeyL gene expression in the sample indicates sensitivity of the cancer tissue to treatment with the agent.

Cancer tissues that are sensitive to treatment with an agent that inhibits Notch receptor activation includes solid tumors such as breast, lung, kidney, colorectal, and pancreatic tumors. Cancer tissues sensitive to treatment with an agent that inhibits Notch receptor activation may also include a body fluid, such as, blood, and bone marrow.

BRIEF DESCRIPTION OF THE DRAWINGS

FIG. 1 is a scatter plot illustrating a linear regression trend line. Linear regression analysis indicates a high degree of correlation between HeyL mRNA expression as determined by qRT-PCR, and response of human colon cancer cell lines to inhibition of Notch receptor activation. Among seven human colon cancer cell lines tested, the $R^2$ value was 0.8699, with p 0.0022. This indicates that the greater the level of HeyL expression relative to Reference (ratio), the greater the sensitivity of the cell line to inhibition of Notch receptor activation. Solid line indicates linear regression; dashed lines indicate 95% confidence interval. Reference is commercially available Universal Human Reference RNA (Stratagene Cat. No. 740000).

FIG. 2 is a scatter plot illustrating a linear regression trend line. Linear regression analysis indicates a high degree of correlation between HeyL mRNA expression as determined by qRT-PCR, and response of human pancreatic cancer cell lines to inhibition of Notch receptor activation. Among seven human colon cancer cell lines tested, the $R^2$ value was 0.6123, with p=0.0026. This indicates that the greater the level of HeyL expression, the greater the sensitivity of the cell line to inhibition of Notch receptor activation. Solid line indicates linear regression; dashed lines indicate 95% confidence interval. Reference is commercially available Universal Human Reference RNA (Stratagene Cat. No. 740000).

FIG. 3 is a microarray expression profile. Microarray analysis of HeyL expression in mouse tumors in which Notch1 is activated by proximal Mo-MuLV integration and which are dependent upon Notch receptor activation are compared to mouse tumors driven by Mo-MuLV integrations that activate genes that do not directly affect Notch receptor activation and which are not dependent upon Notch receptor activation. Results such as these indicate that Notch-dependent tumors express significantly higher levels of HeyL than tumors that are not dependent upon Notch receptor activation ($p=8.5\times10^{-7}$).

DETAILED DESCRIPTION OF THE INVENTION

Biomarkers

There are three distinct types of cancer biomarkers: (1) prognostic biomarkers, (2) predictive biomarkers, and (3) pharmacodynamic (PD) biomarkers. A prognostic biomarker is used to classify a cancer, e.g., a solid tumor, according to aggressiveness, i.e., rate of growth and/or metastasis, and refractiveness to treatment. This is sometimes called distinguishing "good outcome" tumors from "poor outcome" tumors. A predictive biomarker is used to assess the probability that a particular patient will benefit from treatment with a particular drug. For example, patients with breast cancer in which the ERBB2 (HER2 or NEU) gene is amplified are likely to benefit from treatment with trastuzumab (HERCEP-TIN®), whereas patients without ERBB2 gene amplification are unlikely to benefit from treatment with trastuzumab. A PD biomarker is an indication of the effect(s) of a drug on a patient while the patient is taking the drug. Accordingly, PD biomarkers often are used to guide dosage level and dosing frequency, during the early stages of clinical development of a new drug. For a discussion of cancer biomarkers, see, e.g., Sawyers, 2008, *Nature* 452:548-552.

The work described herein demonstrates that HeyL is a predictive biomarker and that an elevated level of HeyL gene expression indicates sensitivity of a tumor to treatment with an inhibitor of Notch signaling. The level of HeyL gene expression (relative to a suitable standard) can be used, in the absence of other gene expression data, as a biomarker for classifying tumors according to their likelihood of responding to treatment with an inhibitor of Notch signaling. Such classification of tumors is useful for treating human patients in a clinical setting. Such classification also is useful for laboratory research involving experimental animals, e.g., genetically engineered mouse models of cancer.

DEFINITIONS

As used herein, an "elevated level" of HeyL gene expression means a level of HeyL gene expression, measured at the RNA level or the protein level, that is significantly higher than a suitable standard of comparison, i.e., a baseline value.

As used herein, "HeyL gene" means: (a) a human gene that encodes the polypeptide consisting of SEQ ID NO: 1 (Accession No. NP_055386); (b) allelic variants of (a); and (c) mammalian orthologs of (a).

As used herein, "Notch ligand" means JAG1, JAG2, DLL1, DLL3, DLL4, or DNER.

As used herein, "Notch receptor" means Notch1, Notch2, Notch3 or Notch4.

As used herein, "Notch receptor activation" means the regulated, site-specific proteolytic cleavage of a Notch receptor that releases the Notch cytoplasmic domain for translocation to the nucleus. Examples of proteins that regulate Notch proteolytic cleavage include: the Notch ligands (JAG1, JAG2, DLL1, DLL3, DLL4, and DNER), Adam10, Adam17, presenilin, nicastrin (NCT), PEN2, APH1 and Crumbs.

As used herein, a "standard value" means a suitable standard of comparison, namely a baseline value against which a measured level of HeyL gene expression is compared, to determine whether the measured level of HeyL gene expression is an elevated level.

HeyL and Notch

The human gene known as HeyL (hairy/enhancer-of-split related with YRPW motif-like) encodes a 328-amino acid polypeptide and belongs to the HESR (hairy and enhancer of split-related) family of basic helix-loop-helix (bHLH) type transcription factors. Together with Hey1 and Hey2, HeyL belongs to the HERP (HES-related repressor protein) subfamily within the HESR family. In common with Hey1 and Hey2, the HeyL protein contains conserved bHLH and Orange domains. HeyL is a downstream effector of Notch signaling and is said to be frequently over-expressed in breast cancers. HeyL is said to target (transcriptionally) the cell cycle inhibitor p15, reducing the effect of p15 and increasing the rate at which cells progress through the cell cycle. See, e.g., WO 2007/136856. The HERP and HES families are closely related, structurally and functionally, but only HeyL, and not any of the other HES family genes or Hey1 or Hey2, serves as a biomarker of sensitivity to inhibition of Notch signaling in the indicated cancers.

Numerous studies have suggested targeting the Notch pathway in cancer treatment. See, e.g., Miele et al., 2006, *Current Cancer Drug Targets* 6:313-323. In most of these studies, the status of various downstream transcriptional targets of the Notch pathway (including Hes1, Hes5, Hey1, Myc, Cyclin D1, Deltex, Nrarp and NFkB) has been used as a surrogate marker for the level of Notch signaling in the cells of interest. Elevated expression of such downstream targets has been interpreted as indicating an active Notch pathway (increased Notch signaling), and decreased expression of such targets has been interpreted as indicating decreased Notch signaling, with the various downstream targets being essentially equivalent in terms of indicating the level of Notch activity (signaling) in a given tissue or cell line. This is demonstrated by publications such as Iso et al., 2002, *J. Biol. Chem.* 277:6598-6607; Dumortier et al., 2006, *Mol. Cell Biol.* 26:209-220; Fischer et al., 2007, *Nuc. Acids Res.* 35:4583-4596; and Leong et al., 2007, *J. Exp. Med.* 204:2935-2948.

In general, in any cell line in which the Notch pathway is active, inhibiting Notch receptor activation will lead to decreased expression of downstream target genes. Importantly, however, the inventors have found that inhibition of Notch receptor activation does not inhibit proliferation (or reduce viability) of all cell lines in which the pathway is active. For example, inhibition of Notch activation by a gamma-secretase inhibitor decreases expression of Notch target genes in both HT-29 and LS-1034 colon cancer cell lines. However, while LS-1034 cells are highly Notch dependent on Notch activation, HT-29 cells are relatively insensitive to inhibition of Notch activation. This shows that reliance on elevated expression of a panel of Notch pathway target genes to identify Notch dependent cell lines is ineffective. It is necessary to identify specific biomarkers, the expression of which correlates with reduced proliferation and/or reduced viability of the cells in response to a Notch receptor activation inhibitor.

HeyL gene expression correlates (positively) with sensitivity of cells to inhibition of Notch receptor activation (dependence upon Notch signaling), whereas expression levels of other individual Notch target genes, or combinations of Notch target genes, do not correlate with such sensitivity. Instead, they merely indicate that the Notch pathway is active. This means that demonstration of Notch pathway activity or Notch signaling in a cell or tissue, is insufficient for predicting that the cell or tissue will be sensitive to treatment with an inhibitor of Notch receptor activation. HeyL differs from other Notch target genes because not only does it indicate Notch pathway activity (or lack thereof), it also indicates sensitivity (or lack thereof) to an inhibitor of Notch receptor activation.

Analysis of expression profile data from human primary tumors reveals variation in HeyL gene expression levels among various cancer types. In addition, these data show that elevation of HeyL gene expression marks human cancers whose growth depends on Notch pathway signaling (and whose growth will be inhibited by agents, whether small molecules or biologics, that inhibit Notch receptor activation). Human cancers with significant variation in HeyL gene expression levels include cancers of the pancreas, breast (particularly basal-like breast cancers) and colon and small cell lung cancers. Notch1 mutant T-ALL also exhibit high HeyL expression. These cancers represent likely contexts in which HeyL gene expression will be a biomarker that predicts sensitivity to inhibition of Notch receptor activation. In other contexts, such as glioblastoma (GBM) cell lines, HeyL is not expressed at a significant level, and there is no significant variation in HeyL gene expression levels among GBM cell lines. Moreover, treatment of GBM cell lines with Notch antagonists, such as Jag1-Fc, identifies Notch-dependent human GBM cell lines, but HeyL expression shows no correlation with GBM cell line sensitivity to inhibition of Notch signaling. Therefore, HeyL can be used in specifically defined tumors as a biomarker of sensitivity to inhibition of the Notch pathway.

Before the present invention, the expression level of any one particular downstream target of Notch has not been shown to predict the sensitivity of a particular cancer, e.g., a particular tumor, to a Notch pathway inhibitor. The inventors have discovered that, surprisingly, in certain cancers, (a) the level of HeyL gene expression is a predictive biomarker for sensitivity to treatment with an inhibitor of Notch receptor activation, and (b) other downstream targets of Notch, such as Hey1 and Hey2, individually or as a group, are not predictive biomarkers for sensitivity to treatment with an inhibitor of Notch receptor activation.

Inhibitors of Notch Receptor Activation

Various agents that inhibit Notch receptor activation are known. For example, small molecule inhibitors of the TNFα converting enzymes (TACE inhibitors), including ADAM10 and ADAM17 (Moss et al., 2008, *Curr Pharm Biotechnol.* 9:2-8), and gamma-secretase inhibitors (DeStrooper et al., 1999, *Nature* 398:518-522) inhibit Notch receptor activation by inhibiting proteolytic cleavage of the Notch receptor. Soluble receptor decoys that sequester Notch ligands can be used to inhibit Notch receptor activation (Funahashi et al., 2008, *Cancer Res.* 68:4727-4735). Also, soluble ligands that inhibit ligand binding to Notch receptors (Noguera-Troise et al., 2006, *Nature* 444:1032-1037) can be used. Antibodies that bind to Notch ligands (Ridgway et al., 2006, *Nature* 444:1083-1087; Noguera-Troise et al., supra) or to Notch receptors (Li et al., 2008, J. Biol. Chem IEP Jan. 8, 2008) can be used to inhibit Notch receptor activation. In addition, antibodies that bind to components of the gamma-secretase complex, e.g. nicastrin, can be used.

Providing Tissue Sample

Methods of the present invention involve providing a sample from a cancerous tissue in a mammal, e.g., a laboratory mouse or a human patient, so the level of HeyL gene expression can be determined in the sample. The form of the sample and the method of obtaining the sample will depend on the type of cancerous tissue involved.

For example, if the cancerous tissue is the blood, as in acute lymphoblastic leukemia, the sample can be a bone marrow sample, which can be obtained using conventional bone marrow biopsy instruments and procedures. Alternatively, the sample can be a sample of the blood itself, which can be obtained using conventional phlebotomy instruments and procedures. Optionally, total blood cells, or certain types of blood cells, e.g., leukocytes, can be isolated for determination of HeyL gene expression.

If the cancerous tissue is a solid tumor, e.g., a carcinoma, sarcoma, glioma or lymphoma, the sample is a tumor sample, which can be obtained by using conventional tumor biopsy instruments and procedures. Endoscopic biopsy, excisional biopsy, incisional biopsy, fine needle biopsy, punch biopsy, shave biopsy and skin biopsy are examples of recognized medical procedures that can be used by those of skill in the art to obtain tumor samples for use in practicing the methods of the invention.

Determining Level of HeyL Gene Expression

In practicing the present invention, determining the level of HeyL gene expression can be performed by any suitable method, e.g., mRNA-based methods or protein-based methods. Various methods of determining the level of expression of a gene of interest are known in the art. Such methods generally can be applied in determining the level of HeyL gene expression. For purposes of the present invention, HeyL gene expression can be determined at the mRNA level or at the polypeptide level.

To assess the relative level of HeyL gene expression, the level of HeyL gene expression in a cancer tissue sample can be subjected to one or more of various comparisons. In general, it can be compared to: (a) HeyL gene expression level(s) in normal tissue from the organ in which the cancer originated; (b) HeyL gene expression levels in a collection of comparable cancer tissue samples; (c) HeyL gene expression in a collection of normal tissue samples; or (d) HeyL gene expression level in an arbitrary standard.

For example, an elevated level of HeyL gene expression in a spontaneous mouse breast tumor could be a level significantly higher than the average level of HeyL gene expression in a reference collection of spontaneous mouse breast tumors in which the level of HeyL gene expression was measured by the same method, such as quantitative PCR. In a second example, an elevated level of HeyL expression in a human basal-like breast cancer tissue sample could be a level significantly higher than the average level of HeyL gene expression in a reference collection of human basal-like breast cancer tissue samples in which the level of HeyL gene expression was measured by the same method, such as immunohistochemistry.

The comparison can be an indirect comparison, as well as a direct comparison. Accordingly, the level of HeyL expression in a tissue sample can be expressed relative to an arbitrary standard, such as the level of HeyL expression in a particular cultured cell line, against which tissue samples of the same type have been compared. In some embodiments of the invention, an elevated level of HeyL gene expression is at least 2-fold higher than the level of HeyL gene expression in an arbitrary standard such as a pool of total RNA from ten human cancer cell lines, which is commercially available as Universal Human Reference RNA (Stratagene Cat. No. 740000).

HeyL mRNA Measurement

Examples of methods for determining the level of HeyL gene expression at the mRNA level include conventional microarray analysis and quantitative polymerase chain reaction (QPCR). RNA can be extracted from the cells, tumor or tissue of interest using standard protocols.

Microarray

The level of mRNA for multiple genes can be determined using conventional microarray expression profile analysis. Instruments, microarray chips, reagents and protocols are known in the art and available from commercial sources. RNA isolated from the samples of interest can be isolated and converted to the labeled material necessary for any specific microarray platform using the manufacturer's protocols, e.g., Agilent or Affymetrix. Microarray hybridizations can be quantified to determine the relative level of expression of every gene that is represented by a probe on the microarray. Comparisons can be conducted between different genes within a single sample, or between the same gene among multiple samples, including control samples.

Quantitative PCR

The level of mRNA for specific genes, including HeyL, can be measured using conventional quantitative RT-PCR technology. Guidance concerning the processing of tissue samples for quantitative PCR is available from various sources. When quantitative PCR is employed in practicing the present invention, primers specific to the gene of interest, e.g., human HeyL, are based on the cDNA sequence of the gene. Commercial technologies such as SYBR green or TaqMan™ can be used in accordance with the vendors' instructions. Messenger RNA levels can be normalized for differences in loading among samples by comparing the levels of housekeeping genes such as B-actin or GAPDH. The level of mRNA expression can be expressed relative to any single control sample such as mRNA from normal, non-tumor tissue or cells. Alternatively, it can be expressed relative to mRNA from a pool of tumor samples, or tumor cell lines, or from a commercially available set of control mRNA (e.g., reference RNA commercially available from Stratagene).

Design and use of suitable PCR primers is known in the art. For use in amplification (PCR) primers preferably are about 17 to 25 nucleotides in length. Primers can be designed to have a particular melting temperature (Tm), using conventional algorithms for Tm estimation. Software for primer design and Tm estimation are available commercially or on the internet, e.g., Primer Express (Applied Biosystems), and Primer3 (Massachusetts Institute of Technology).

HeyL Protein Measurement

Examples of methods for determining the level of HeyL gene expression at the protein level include enzyme linked immunosorbent assay (ELISA) and immunohistochemistry (IHC).

ELISA

Performing a HeyL ELISA requires at least one anti-HeyL antibody, i.e., the detection antibody. HeyL protein from a sample to be analyzed is immobilized on a solid support such as a polystyrene microtiter plate. This immobilization can be by non-specific binding of the HeyL, i.e., through adsorption to the surface. Alternatively, immobilization can be by specific binding, i.e., through binding of HeyL protein from the sample by a capture antibody (anti-HeyL antibody different from the detection antibody), in a "sandwich" ELISA. After the HeyL is immobilized, the detection antibody is added, and the detection antibody forms a complex with the bound HeyL. The detection antibody is linked to an enzyme, either directly or indirectly, e.g., through a secondary antibody that specifically recognizes the detection antibody. Typically between each step, the plate, with bound HeyL, is washed with a mild detergent solution. Typical ELISA protocols also include one or more blocking steps, which involve use of a non-specifically-binding protein such as bovine serum albumin to block unwanted non-specific binding of protein reagents to the plate. After a final wash step, the plate is developed by addition of an appropriate enzyme substrate, to produce a visible signal, which indicates the quantity of HeyL in the sample. The substrate can be, e.g., a chromogenic substrate or a fluorogenic substrate. ELISA methods, reagents and equipment are well-known in the art and commercially available.

Immunohistochemistry (IHC)

Assaying HeyL by IHC requires at least one anti-HeyL antibody. Using standard approaches the anti-HeyL antibody can be used to detect the presence of HeyL protein in sections obtained from tumors, including paraffin-embedded and frozen tumor sections. Typically, the tumor sections are initially treated in such a way as to retrieve the antigenic structure of proteins that were fixed in the initial process of collecting and preserving the tumor material. Slides are then blocked to prevent non-specific binding by the anti-HeyL detection antibody. The presence of HeyL protein is then detected by binding of the anti-HeyL antibody to the HeyL protein. The detection antibody is linked to an enzyme, either directly or indirectly, e.g., through a secondary antibody that specifically recognizes the detection antibody. Typically, the tumor sections are washed and blocked with non-specific protein such as bovine serum albumin between steps. The slide is developed using an appropriate enzyme substrate to produce a visible signal, and the samples are then counterstained with hematoxylin.

Confidence Levels

Elevated HeyL expression is not only a qualitative biomarker of sensitivity to Notch antagonists. The present invention also provides for the use of HeyL expression level as a quantitative biomarker. The higher the level of HeyL gene expression: (a) the greater the confidence with which one can predict sensitivity, and (b) the greater the degree of sensitivity to Notch antagonists.

The degree of confidence with which HeyL expression levels can be used to predict sensitivity to a Notch pathway inhibitor can be determined using a number of approaches. In one instance, the degree of correlation between HeyL expression level and sensitivity of human cancer cells to Notch antagonists can be determined using linear regression analyses to compare the 2 variables. For example, in human colon cancer cell lines there is a very strong correlation between HeyL expression level and sensitivity to Notch antagonists ($R^2=0.87$, $p=0.0022$). Similarly, in human pancreatic cancer cell lines there is a very strong correlation between HeyL expression level and sensitivity to Notch antagonists ($R^2=0.61$, $p=0.0026$). These data indicate that the greater the level of HeyL expressed the greater the sensitivity to Notch antagonists. In a second instance, samples can be classified into 3 groups—high expression of HeyL (at least 2× above reference), mid-level HeyL expression (less than 2× greater than reference, but more than 0.5× reference) or low HeyL expressors (less than 0.5× reference). In this case, the correlation of the level of HeyL expression and the degree of sensitivity to Notch antagonists can be calculated using Cohen's kappa, a statistical measure of inter-rater agreement. Classification of 23 human pancreatic, colon, breast, SCLC and T-ALL cancer cell lines into high, medium and low levels of HeyL expression predicts with very high confidence (Cohen's kappa=0.877) cell lines that will show a high, medium and low degree, respectively, of sensitivity to Notch antagonists.

EXAMPLES

The invention is further illustrated by the following examples. The examples are provided for illustrative purposes only, and are not to be construed as limiting the scope or content of the invention in any way.

Example 1

Jag1-Fc Inhibitor

Soluble forms of Notch ligand extracellular domains (ECDs) previously have been shown to interfere with the binding of normal Notch ligands to Notch receptors, thereby acting as antagonists of Notch signaling. Therefore, a soluble form of the Notch ligand Jag1 was constructed for use in experiments described below. This was done by using PCR to amplify the extracellular domain of human Jagged1 and join it to the Fc domain from human IgG1. The construct was cloned into the pEE14.4 vector (Lonza), transfected into CHOK1SV cells and selected to make stable expressing clones. Jag1-Fc protein was purified from the cell supernatant, quantified, and frozen at −80° C. until use.

Example 2

Proliferation Assays with Soluble Jag1-Fc Inhibitor

Proliferation assays with soluble Jag1-Fc inhibitor were performed for the following cell lines: HPAC, Panc10.05, PL45, PANC-1, CAPAN-1, CAPAN-2, AsPC-1, HPAF II, SW1990, BxPC-3, MiaPaCa-2, Hs766T (pancreatic cancer cell lines); HCT-116, LS-1034, SW-480, DLD1, HCT-15, HT-29, COLO-205 (colon cancer cell lines); DU4475, MCF12A (breast cancer cell lines); Karpas45 (T-ALL cell line); and NCI-H187 (lung cancer cell line).

The following protocol was used for all cell lines. To identify Notch-dependent human cancer cell lines, we utilized the soluble extracellular domain (ECD) of JAG1 fused to the human IgG1 Fc region. Proliferation and viability of human cancer cell lines was examined in the absence and presence of Jag1-Fc, to determine the effect of inhibition of Notch signaling on proliferation and viability of human cancer cell lines.

For proliferation assays, all human cancer cell lines were cultured in the appropriate medium with a final concentration of 2% fetal bovine serum (FBS). Optimal seeding densities for each cell line was determined such that cells did not reach greater than 70-80% confluence prior to the end of the assay. Cells were plated in 96-well plates in triplicate at the appropriate cell density, after which Jag1-Fc (diluted in serum-free media) was added to give a final concentration of 100, 50, or 25 µg/mL of the soluble ligand. Purified GP120 antibody, mouse IgG and serum-free media were used as negative controls. Cells were allowed to proliferate for 48 hours, then assayed by MTT (Thiazolyl Blue Tetrazolium Bromide) or BrdU assays (Roche).

For MTT assays, MTT was resuspended in PBS (at 5 mg/ml) and filtered through a 0.2 µm filter. 10 µl of MTT was added to cells (treated with soluble ligands or controls in a final volume of 100 µl) 48 hours post-treatment, allowed to incubate for 4 hours, then stopped by addition of 90 µl 0.01N HCl/10% SDS. MTT was also added to a small number of wells at the time of seeding to determine starting cell number. After overnight incubation at 37° C., plates were read on a Molecular Devices-Spectromax m2 at [A570-A690]. For BrdU assays, cells were allowed to proliferate for 48 hours, then labeled with BrdU for either 5 or 24 hours before fixing cells and processing according to the manufacturer's protocol. The percent response of each cell line to inhibition of Notch signaling by Jag1-Fc was quantified by comparison to the cell number seeded at the start of the assay (MTT assay) or by comparison to the background signal (BrDU assay).

In parallel, RNA was collected from the same set of cell lines while they were growing under standard culture conditions, in the absence of any inhibitors of the Notch pathway. Cancer cell lines were cultured in the appropriate medium supplemented with 10% FBS+1% Pen/Strep and harvested by trypsinization when ~70% confluent. RNA was obtained by using the RNeasy Mini Kit (Qiagen) and diluted to 10 ng/µl for use with the Quantitect SYBR Green RT-PCR kit (Qiagen). To compare expression levels relative to other human cancer cell lines, 10 ng/µl Universal Human Reference RNA (Stratagene) was also amplified using primers for each target gene. Amplification of the beta-actin gene was also performed to enable normalization of expression across cell lines. The relative level of expression among the human cancer cell lines of the following Notch pathway genes was determined by qRT-PCR: Notch1, Notch2, Notch3, Notch4, Jag1, Jag2, DLL1, DLL3, DLL4, Hes1, Hes5, Hes6, Hes7, Hey1, Hey2, HeyL, and Helt.

Figure 1:
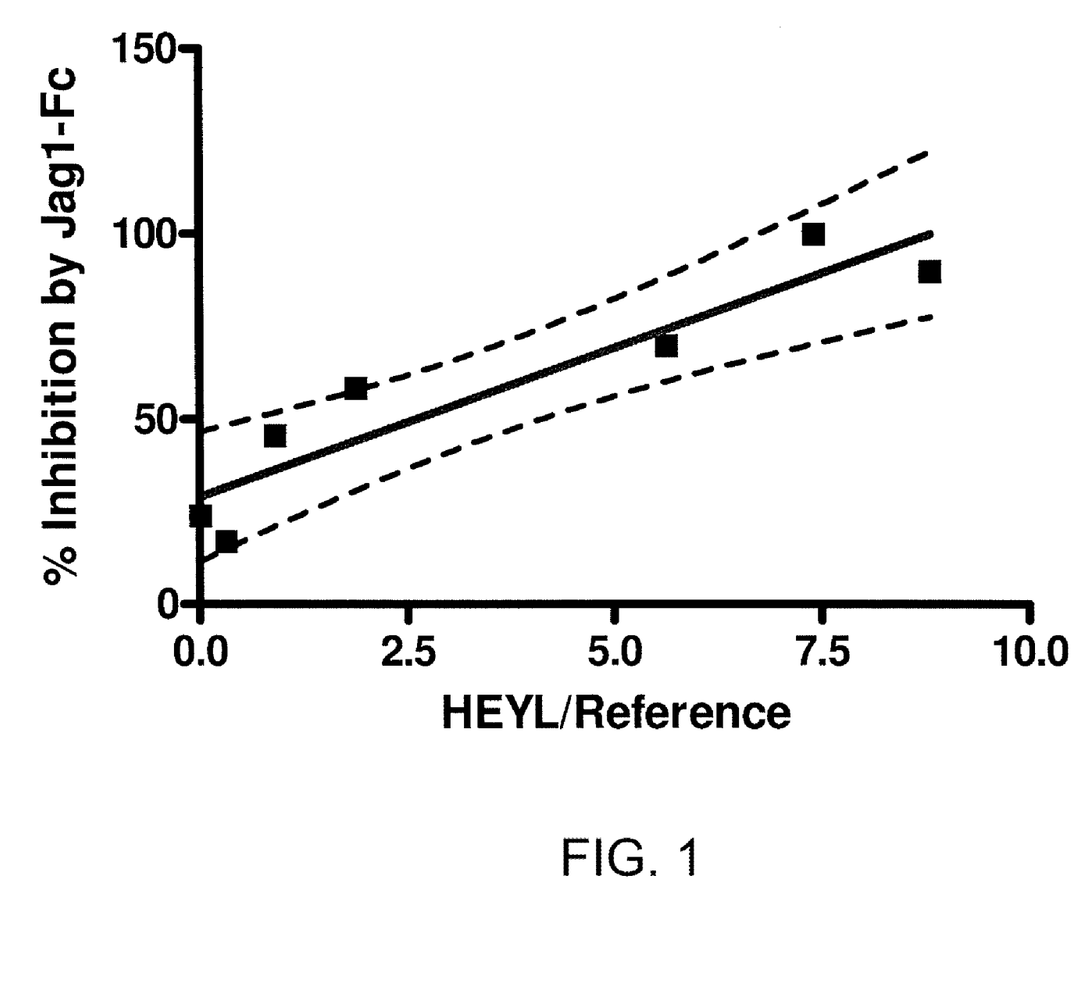
Figure 2:
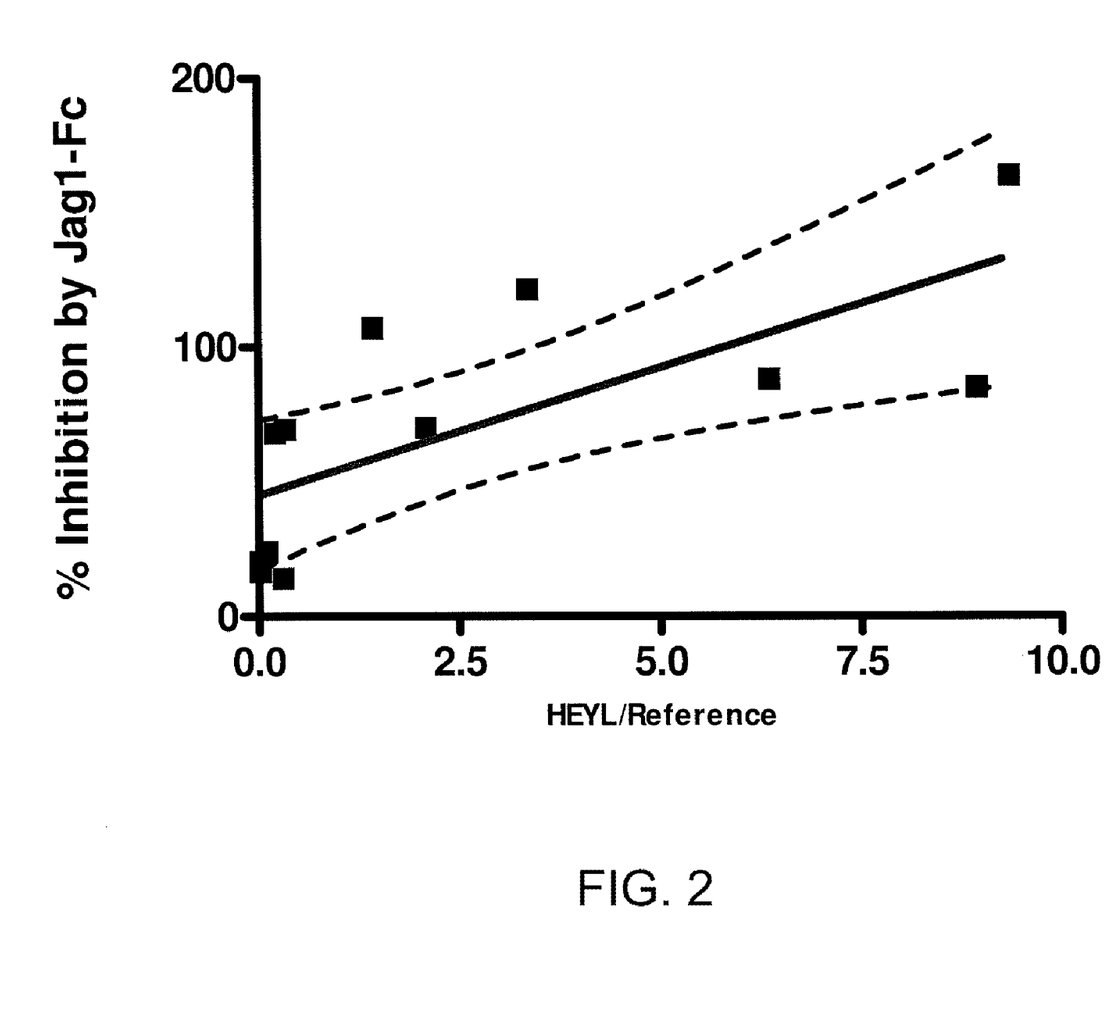

Comparison of Notch pathway gene expression with the effect of Jag1-Fc on proliferation the human cancer cell lines indicated that there was a high degree of correlation between expression of HeyL and sensitivity to Jag1-Fc inhibition. A Cohen's kappa value of 0.877 was calculated for this correlation, indicating a very high degree of confidence that HeyL level is correlated with response to Jag1-Fc. Moreover, linear regression analysis indicates a high degree of correlation between HeyL expression and sensitivity to inhibition of the Notch pathway for human colon cancer cell lines ($R^2$=0.87, p=0.0022) (FIG. 1) and pancreatic cancer cell lines ($R^2$=0.61, p=0.0026) (FIG. 2).

No correlation between expression level and response to inhibition of Notch signaling was observed for any of the other genes examined. This indicated that elevated HeyL gene expression is a specific biomarker of sensitivity to inhibition of Notch pathway signaling.

The correlation of elevated HeyL gene expression with sensitivity to inhibition of Notch receptor activation was observed with respect to other cell lines in addition to colon and pancreatic cancer cells. For example, a significant positive correlation between elevated HeyL gene expression and sensitivity to inhibition of Notch receptor activation was observed in human breast cancer cells. DU4475 cells are highly sensitive to inhibition of Notch receptor activation and express the highest level of HeyL among 51 human breast cancer cell lines tested. In contrast, MCF12A cells are not dependent upon Notch, and they express the lowest level of HeyL among the same set of 51 human breast cancer cell lines tested. Human T-ALL cells (Karpas 45) and lung cancer cells (NCI-H187) exhibited elevated levels of HeyL gene expression and also were sensitive to inhibition of Notch receptor activation.

No correlation was observed between sensitivity to inhibition of Notch receptor activation and HeyL expression among 9 glioblastoma cell lines, suggesting that HeyL expression level is not a biomarker of sensitivity to inhibition of Notch receptor activation in this specific tumor type.

Example 3

Treatment of Cells with γ-Secretase Inhibitor

Cells were seeded into 6-well plates in 2 mL of media. Replicates wells of cells treated with 1 µM, 3 µM, and 6 µM Gamma Secretase Inhibitor (GSI; Sigma L-685,458) or DMSO (Sigma D2650) (vehicle control) immediately after seeding. Cells were incubated at 37° C. 5% $CO_2$ for 20 hours after treatment, then collected, rinsed with PBS (Invitrogen 14040-133), and cell pellets were frozen on dry ice and stored at −80° C. Subsequently, RNA was prepared by hand using the Qiagen RNeasy™ miniprep columns (Qiagen GR8RNA) and qRT-PCR performed to analyze Notch target gene expression according to standard protocol (Qiagen Quantitect SYBR GREEN RT-PCR kit 204245). Quantitative RT-PCR was run on Applied Biosystems 7900HT Sequence Detection System. Results were analyzed using the comparative Ct method. Beta Actin was used as the housekeeping gene and Stratagene Universal Human Reference RNA (Stratagene Cat. No. 740000) was used as an external reference sample to determine the level of expression of the Notch target genes Hes1, Hes5, Hes6, Hes7, Hey1, Hey2, HeyL, and Helt.

To measure cell proliferation and viability HT29 and LS1034 cells were harvested with 0.25% trypsin (GIBCO Cat. No. 25200), resuspended in RPMI media (GIBCO Cat. No. 11875) containing 10% FBS (GIBCO Cat. No. 10438) and 1% pen/strep, and then counted. Cells were centrifuged and washed with serum-free RPMI, and then re-suspended at $1.2 \times 10^5$ cells/mL in RPMI media with 4% FBS and 1% pen/strep. Both HT29 and LS1034 cells were ultimately seeded at 6K per well (50 µL/well of cell suspension) in 96-well plates (Costar Cat. No. 3595). Fifty microliters of either vehicle control or an inhibitor of Notch receptor activation was added to the cells in triplicate, so that the final concentration of FBS in each well was 2%. In these experiments Jag1-Fc or gamma-secretase inhibitor (GSI; Sigma L-685,458) were used as inhibitors of Notch receptor activation.

DMSO, the vehicle control for GSI, was prepared as follows: 1.0, 0.5, 0.25 and 0.1% DMSO were prepared as 2× solutions in serum-free RPMI. Untreated cells were given serum-free RPMI. GSI dilutions were prepared as follows from a 1 mM stock in DMSO: 1.0, 2.5, 5, and 10 µM GSI dilutions were prepared as 2× solutions in serum-free RPMI. RPMI media (100 µL/well) was added to the outside row of wells on the 96 well-plate to prevent evaporation of test wells. Treatment with Jag1-Fc, and all MTT assays to measure cell proliferation were performed as described above.

These analyses indicated that inhibition of the Notch pathway resulted in complete growth inhibition and cell death of LS-1034 cells (>100% growth inhibition), but had only a modest effect on proliferation of HT-29 cells (<17% growth inhibition).

Human cancer cell lines which are Notch-dependent were also demonstrated to exhibit elevated levels of HeyL when grown in vivo as xenografts in immunocompromised mice. For example, the T-ALL cell line, Karpas45, which is very sensitive to inhibition of Notch signaling, and which expresses elevated levels of HeyL in culture, was also shown (by immunohistochemical staining of sections of Karpas45 xenograft tumors) to express elevated levels of HeyL in tumors, in comparison to normal tissue in vivo.

Tumors of interest were fixed in 10% buffered formalin and embedded in paraffin. 4 µM thick sections were sliced using a microtome. Slides were warmed at 55° C. for 10 minutes before de-paraffinizing in xylene using 2× five minute incubations. Sections were hydrated in decreasing concentrations of ethanol (100%, 95%, 70%) with 2× two minute washes for each step. Endogenous peroxidase was quenched by incubating in 0.3% $H_2O_2$ for 30 minutes. Slides were heated in citrate buffer, pH 6.0 for 3× five minutes in a microwave oven (medium power level), then blocked in 10% goat serum for 20 minutes. For immune-staining, primary and isotype control antibodies (rabbit IgG, Epitomics) were made up in 1% FBS at 4 µg/mL and incubated for 30 to 45 minutes. Secondary antibodies (goat α-rabbit biotinylated, Vector Labs) were diluted at 1:200 in 1% FBS and incubated for 30 to 45 minutes. The Vectastain Standard ABC kit (Vector Labs) was used according to the manufacturer's instructions. Slides were incubated with DAB enzyme substrate for 5 minutes (Vector Labs) and with DAB enhancing solution for 2 minutes (Zymed). Samples were counterstained with Mayers hematoxylin for 1 minute, then dehydrated with 2×2 minute incubations in increasing concentrations of ethanol (70%, 95%, 100%), followed by xylene for 2×5 minutes before being sealed with cover slips.

When using anti-human mouse monoclonal antibodies (Abcam Cat. No. ab61277) the Vector M.O.M. (mouse-on-mouse) kit (Vector Labs) was used to reduce/eliminate non-specific staining of host tissue for tumors grown as a mouse xenograft model. Tumors were sectioned and deparaffinized as described above, then incubated with M.O.M mouse IgG blocking reagent for 60 minutes. For immunostaining, primary and isotype control (mouse IgG, Sigma) were made up in M.O.M. diluent at 10 µg/mL and incubated for 30 minutes.

Secondary antibodies (anti-mouse biotinylated, M.O.M. kit, Vector Labs) were made up in M.O.M. diluent and incubated for 30 minutes. Detection, counterstaining, and dehydration were performed as described above.

HeyL gene expression was found to be elevated in mouse tumors that arose spontaneously in response to enhanced expression of Notch1 caused by chromosomal integration of Mo-MuLV near the Notch1 locus. The growth of such tumors was Notch-dependent, as indicated by sensitivity to inhibition by GSI, a gamma-secretase inhibitor (Sigma L-685,458). Mouse tumors that did not exhibit elevated Notch1 expression and were not sensitive to GSI showed significantly lower levels of HeyL gene expression. In general, tumors that displayed Mo-MuLV integration near a gene encoding a Notch receptor and in which elevated expression of the Notch receptor was confirmed by qRT-PCR or microarray expression analysis, also showed elevated HeyL gene expression by comparison to: (1) tumors resulting from Mo-MuLV integration at sites distant from the Notch loci in which there is no retroviral-induced upregulation of Notch receptor expression; and (2) spontaneous breast tumors in Ink4a-null mice overexpressing an exogenous Her2 oncogene driven by an MMTV promoter. Two-tailed student T-test indicated a highly significant elevation of HeyL gene expression in Notch-dependent tumors by comparison to tumors not driven by Notch pathway activation ($p<1\times10^{-6}$). This correlation between Notch dependence due to retroviral upregulation of Notch receptor expression, and elevated levels of HeyL further demonstrated the role of HeyL gene expression as a biomarker of Notch pathway dependence.

To perform the analyses on the retroviral-induced tumors, tumor-bearing animals were euthanized, tumors were collected and 0.2 g pieces were disaggregated using 4 mg/ml collagenase in RPMI media for 2 hours at 37° C. Cells were further disaggregated by passage through an 18 G needle 5-10 times. Single cells in suspension were aspirated in the supernatant for further analysis.

For cell viability assays, single cells were re-seeded at 100,000 cell per well in 12-well plates in RPMI media supplemented with 10% FBS, 1% PenStrep, and 0.01 µM Beta estradiol. Cells were then treated for 48 hours with 1, 3 or 10 µM GSI (Sigma L-685,458) or vehicle control. Cell viability and apoptosis were assessed using Guava PCA-96 Viacount Flex reagent (Cat. No. 4700-0060) and measured using a Guava PCA-96 instrument, according to manufacturer's protocol. To measure mRNA expression levels, fresh tumor samples were collected, RNA was prepared using standard protocols, and microarray gene expression profile analysis was performed using Agilent cDNA microarray chips according to manufacturer's recommended protocols. Relative expression of HeyL and other genes was calculated by comparison to a universal mouse reference RNA sample from Stratagene (Universal Mouse Reference RNA Cat. No. 740100). Tumors were ranked according to the relative level of HeyL expression, and a student T-test was used to determine the significance of the difference in expression of HeyL in tumors displaying Mo-MuLV integration near a gene encoding a Notch receptor and in which elevated expression of the Notch receptor is confirmed by qRT-PCR or microarray expression analysis, by comparison to tumors lacking retroviral activation of the Notch pathway.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

---

What is claimed is:

1. A method of identifying a human or mouse cancer tissue sensitive to treatment with an agent that inhibits Notch receptor activation, comprising:
   (a) measuring the level of HeyL gene expression in a sample derived from the cancer tissue; and
   (b) comparing the level of HeyL gene expression against a standard value, thereby identifying a cancer tissue sensitive to treatment with an agent that inhibits Notch receptor activation on the basis of HeyL gene expression alone, wherein an elevated level of HeyL gene expression in the sample indicates sensitivity of the cancer tissue to treatment with the agent.

2. The method of claim 1, wherein the cancer tissue is a solid tumor.

3. The method of claim 2, wherein the tumor is selected from the group consisting of a breast tumor, a lung tumor, a kidney tumor, a colorectal tumor, and a pancreatic tumor.

4. The method of claim 1, wherein the cancer tissue is selected from the group consisting of blood and bone marrow.

5. The method of claim 1, wherein the elevated level of HeyL gene expression is at least two-fold, in comparison with the level of HeyL gene expression in a suitable control sample.

6. The method of claim 1, wherein the level of HeyL gene expression is measured detecting mRNA.

7. The method of claim 6, wherein the mRNA detection is by microarray.

8. The method of claim 6, wherein the mRNA detection is by quantitative PCR.

9. The method of claim 5, wherein the level of HeyL gene expression is measured by HeyL polypeptide detection.

* * * * *

UNITED STATES PATENT AND TRADEMARK OFFICE
CERTIFICATE OF CORRECTION

PATENT NO. : 7,544,476 B1 Page 1 of 1
APPLICATION NO. : 12/360790
DATED : June 9, 2009
INVENTOR(S) : Ronan O'Hagan et al.

Figure 3:
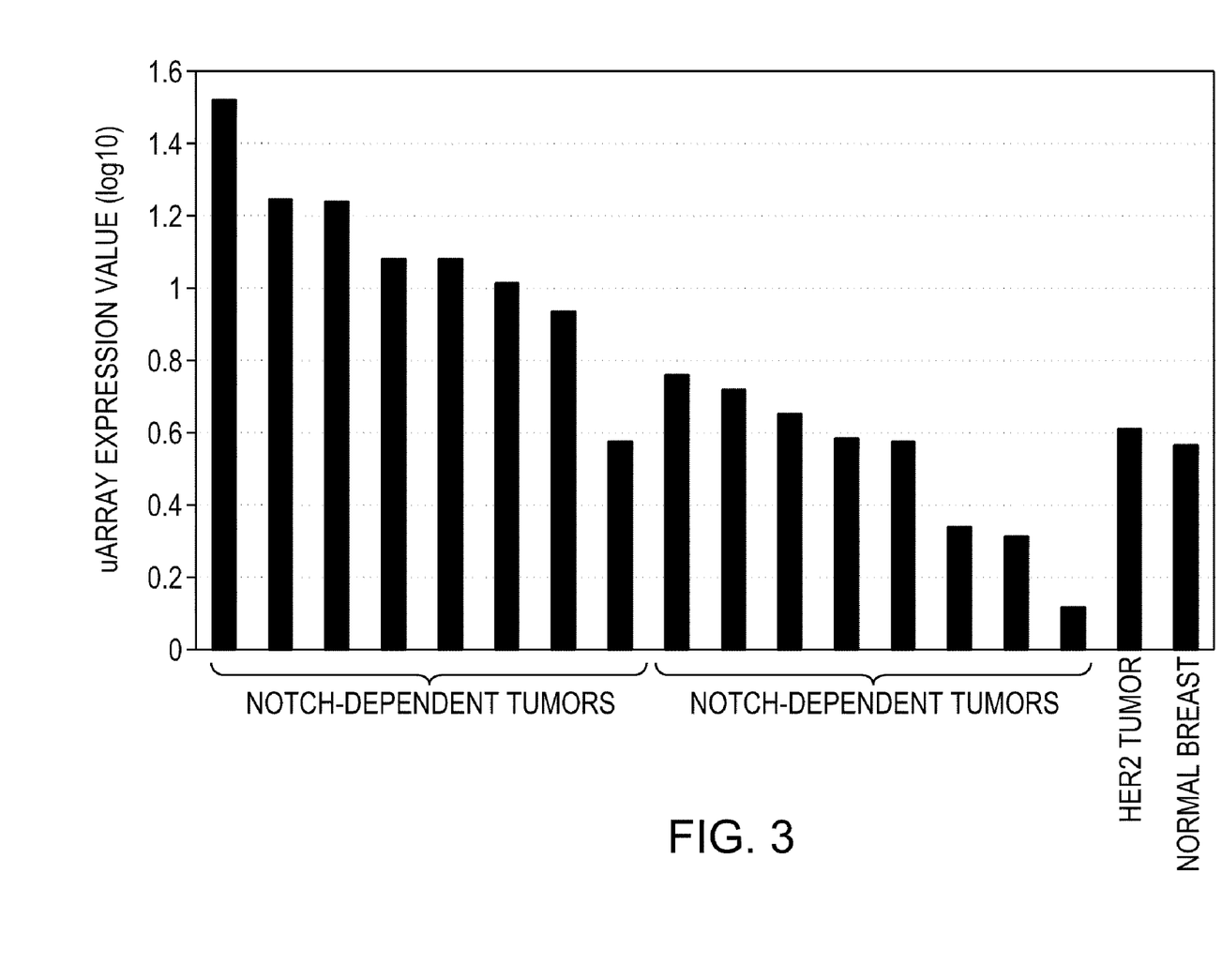

It is certified that error appears in the above-identified patent and that said Letters Patent is hereby corrected as shown below:

In the drawings, Sheet 3, Fig. 3, x-axis, second bracket, replace "Notch-Dependent Tumors" with --Notch-Independent Tumors--, as shown below:

FIG. 3

Signed and Sealed this

Twenty-second Day of September, 2009

David J. Kappos
*Director of the United States Patent and Trademark Office*

SEQUENCE LISTING

```
<160> NUMBER OF SEQ ID NOS: 1

<210> SEQ ID NO 1
<211> LENGTH: 328
<212> TYPE: PRT
<213> ORGANISM: Homo sapiens

<400> SEQUENCE: 1

Met Lys Arg Pro Lys Glu Pro Ser Gly Ser Asp Gly Glu Ser Asp Gly
1               5                   10                  15

Pro Ile Asp Val Gly Gln Glu Gly Gln Leu Ser Gln Met Ala Arg Pro
            20                  25                  30

Leu Ser Thr Pro Ser Ser Ser Gln Met Gln Ala Arg Lys Lys Arg Arg
        35                  40                  45

Gly Ile Ile Glu Lys Arg Arg Arg Asp Arg Ile Asn Ser Ser Leu Ser
    50                  55                  60

Glu Leu Arg Arg Leu Val Pro Thr Ala Phe Glu Lys Gln Gly Ser Ser
65                  70                  75                  80

Lys Leu Glu Lys Ala Glu Val Leu Gln Met Thr Val Asp His Leu Lys
```

-continued

```
                     85                  90                  95
Met Leu His Ala Thr Gly Gly Thr Gly Phe Phe Asp Ala Arg Ala Leu
                100                 105                 110
Ala Val Asp Phe Arg Ser Ile Gly Phe Arg Glu Cys Leu Thr Glu Val
                115                 120                 125
Ile Arg Tyr Leu Gly Val Leu Glu Gly Pro Ser Ser Arg Ala Asp Pro
            130                 135                 140
Val Arg Ile Arg Leu Leu Ser His Leu Asn Ser Tyr Ala Ala Glu Met
145                 150                 155                 160
Glu Pro Ser Pro Thr Pro Thr Gly Pro Leu Ala Phe Pro Ala Trp Pro
                165                 170                 175
Trp Ser Phe Phe His Ser Cys Pro Gly Leu Pro Ala Leu Ser Asn Gln
                180                 185                 190
Leu Ala Ile Leu Gly Arg Val Pro Ser Pro Val Leu Pro Gly Val Ser
            195                 200                 205
Ser Pro Ala Tyr Pro Ile Pro Ala Leu Arg Thr Ala Pro Leu Arg Arg
        210                 215                 220
Ala Thr Gly Ile Ile Leu Pro Ala Arg Arg Asn Val Leu Pro Ser Arg
225                 230                 235                 240
Gly Ala Ser Ser Thr Arg Arg Ala Arg Pro Leu Glu Arg Pro Ala Thr
                245                 250                 255
Pro Val Pro Val Ala Pro Ser Ser Arg Ala Ala Arg Ser Ser His Ile
                260                 265                 270
Ala Pro Leu Leu Gln Ser Ser Ser Pro Thr Pro Pro Gly Pro Thr Gly
            275                 280                 285
Ser Ala Ala Tyr Val Ala Val Pro Thr Pro Asn Ser Ser Ser Pro Gly
        290                 295                 300
Pro Ala Gly Arg Pro Ala Gly Ala Met Leu Tyr His Ser Trp Val Ser
305                 310                 315                 320
Glu Ile Thr Glu Ile Gly Ala Phe
                325
```